US006997938B2

(12) United States Patent
Wang et al.

(10) Patent No.: US 6,997,938 B2
(45) Date of Patent: Feb. 14, 2006

(54) EMBOLIC PROTECTION DEVICE (75) Inventors: Ling Wang, Eden Prairie, MN (US); Martin Willard, Burnsville, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 433 days.

(21) Appl. No.: 10/075,485

(22) Filed: Feb. 12, 2002

(65) Prior Publication Data

US 2003/0153942 A1 Aug. 14, 2003

(51) Int. Cl.
*A61M 29/00* (2006.01)

(52) U.S. Cl. ...................................... 606/200
(58) Field of Classification Search ................ 606/200, 606/194; 623/1.11
See application file for complete search history.

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |

(Continued)

FOREIGN PATENT DOCUMENTS

| | | |
|---|---|---|
| DE | 28 21 048 | 7/1980 |
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |

(Continued)

OTHER PUBLICATIONS

"Atherosclerotic Disease of the Aortic Arch as a Risk Factor of Recurrent Ischemic Stroke," The New England Journal of Medicine, pp. 1216–1221 (May 1996).
"Endovascular Grafts, Stents Drive International Radiology Growth," *Cardiovascular Device Update*, 2(3):1–12 (Mar. 1996).
"Protruding Atheromas in the Thoracic Aortic and Systemic Embolization," pp. 423–427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601–604 (Sep. 1983).

(Continued)

*Primary Examiner*—Tan-Uyen T. Ho
(74) *Attorney, Agent, or Firm*—Crompton, Seager & Tufte LLC (57) ABSTRACT

Catheters for retrieval or delivery of an embolic protection device from the vasculature comprise an outer sheath having a side opening for receiving a guidewire with an embolic protection device at distal end and an inner shaft having a port and a plurality of flush holes in addition to the port. Methods for retrieving and delivering an embolic protection device are disclosed.

27 Claims, 6 Drawing Sheets

U.S. PATENT DOCUMENTS

| | | |
|---|---|---|
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnic et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A * | 12/1999 | Ambrisco et al. .......... 606/200 |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 * | 6/2001 | Addis .................... 606/200 |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,616,681 B1 * | 9/2003 | Hanson et al. .............. 606/200 |
| 2002/0121472 A1 * | 9/2002 | Garner et al. ............... 210/348 |

FOREIGN PATENT DOCUMENTS

| | | |
|---|---|---|
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 177 777 A2 | 7/2001 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |

| | | |
|---|---|---|
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42509 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/45590 A2 | 8/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

Cragg, Andrew et al., "Nonsurgical Placement of Arterial Endoprosthesis: A New Technique Using Nitinol Wire," *AJR*, pp. 261–263 (Apr. 1983).

Diethrich et al., "Percutaneous Techniques for Endoluminal Carotid Interventions," *J. Endovasc. Surg.*, 3:182–202 (1996).

Fadali, A. Moneim, "A filtering device for the prevention of particulate embolization during the course of cardiac surgery," Surgery, 64(3):634–639 (Sep. 1968).

Haissaguerre et al., "Spontaneous Initiation of Atrial Fibrillation by Ectopic Beats Originating in the Pulmonary Veins," *The New England Journal of Medicine*, 339(10):659–666 (Sep. 1988).

Jordan, Jr. et al., "Microemboli Detected by Transcranial Doppler Monitoring . . . ," Cardiovascular Surgery, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arterious After Balloon Dilation: an Experimental Study," Laboratory Investigation, 69(4):772–774 (Apr. 1984).

Marache et al., "Percutaneous Transluminal Venous Angioplasty . . . ," *American Heart Journal*, 125(2 Pt 1):362–366 (Feb. 1993).

Mazur et al., "Directional Atherectomy with the Omnicath™: A Unique New Catheter System," *Catheterization and Cardiovascular Diagnosis*, 31:17–84 (1994).

Moussa, MD, Issaam "Stents Don't Require Systemic Anticoagulation . . . But the Technique (and Results) Must be Optimal," *Journal of Invasive Cardiol.*, 8(E):3E–7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386–392 (1998).

Theron et al., "New Triple Coaxial Catheter System for Carotoid Angioplasty with Cerebral Protection," *American Journal of Neuroradiology*, 11:869–874 (1990).

Tunick et al., "Protruding atherosclerotic plaque in the aortic archo f patients with systemic embolization: A new finding seen by transesophageal echocardiography," *American Heart Journal* 120(3):658–660 (Sep. 1990).

Waksman et al., "Distal Embolization is Common After Directional Atherectomy . . . ," *American Heart Journal*, 129(3):430–435 (1995).

Wholey, Mark H. et al., PTA and Stents in the Treatment of Extracranial Circulation, *The Journal of Invasive Cardiology*, 8(E):25E–30E (1996).

* cited by examiner

EMBOLIC PROTECTION DEVICE

FIELD OF THE INVENTION

The present invention relates generally to devices and methods for treating occluded or stenoic blood vessels. More particularly, the present invention relates to devices and methods for delivering or retrieving an embolic protection device from the vasculature of a patient.

BACKGROUND OF THE INVENTION

Atherosclerosis is a major problem wherein blood vessels become blocked or narrowed. This blockage can result in lack of oxygenation to the heart. It is critical that the heart muscle be well oxygenated so that the blood pumping action of the heart is not impaired.

Occluded or stenotic blood vessels may be treated with a number of medical procedures including, for example, angioplasty and atherectomy. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a balloon catheter. The balloon catheter is advanced over a guidewire such that the balloon is positioned adjacent a stenotic lesion. The balloon is then inflated and the restriction in the vessel is opened. During an atherectomy procedure, the stenotic lesion may be mechanically cut away from the blood vessel wall using an atherectomy catheter.

During atherectomy procedures, stenotic debris that is separated from the stenosis may be free to flow within the lumen of the vessel. If this debris enters the circulatory system, it could block other vascular regions including the neural vasculature, or in the lungs. An occlusion in the neural vasculature may cause a stroke, and an occlusion in the lungs may interfere with the oxygenation of the blood. During angioplasty procedures, stenotic debris may also break loose due to manipulation of the blood vessel. Because of this debris, a number of devices termed embolic protection devices have been developed to filter out this debris.

SUMMARY OF THE INVENTION

The present invention relates generally to devices and methods for treating occluded or stenoic blood vessels. More particularly, the present invention relates to devices and methods for delivering or retrieving an embolic protection device from the vasculature of a patient.

An embodiment of the invention includes a filter retrieval catheter. The filter retrieval catheter may comprise an inner shaft slidably disposed within an outer sheath. The inner shaft may include a proximal end, a mid-region, and a tapered distal end. The distal end may include a tubular member. A guidewire can be adapted to pass through the tubular member of the inner shaft. The guidewire may include an embolic protection device coupled to a distal end thereof.

The outer sheath may further comprise an opening. In addition, a cover sheath may be disposed about the outer sheath, for example over the opening. The cover sheath may further comprise a slot that may allow the guidewire to be disposed therein. Retrieval of the embolic protection device may including shifting the position of the inner shaft relative to the opening in the outer sheath.

Preparation of the retrieval catheter may comprise elimination of air from vacant space between the inner shaft and the outer sheath. Air may be substantially eliminated from the vacant space by flushing the vacant space with a fluid. Fluid can be additionally flushed through the proximal end of the catheter and through the opening. In addition to the vacant spaces, distant vacant spaces may need to be flushed. According to this embodiment, the tubular member may further comprise a plurality of flush holes.

DETAILED DESCRIPTION OF THE INVENTION

The following description should be read with reference to the drawings wherein like reference numerals indicate like elements throughout the several views. The detailed description and drawings represent select embodiments and are not intended to be limiting.

Figure 1:
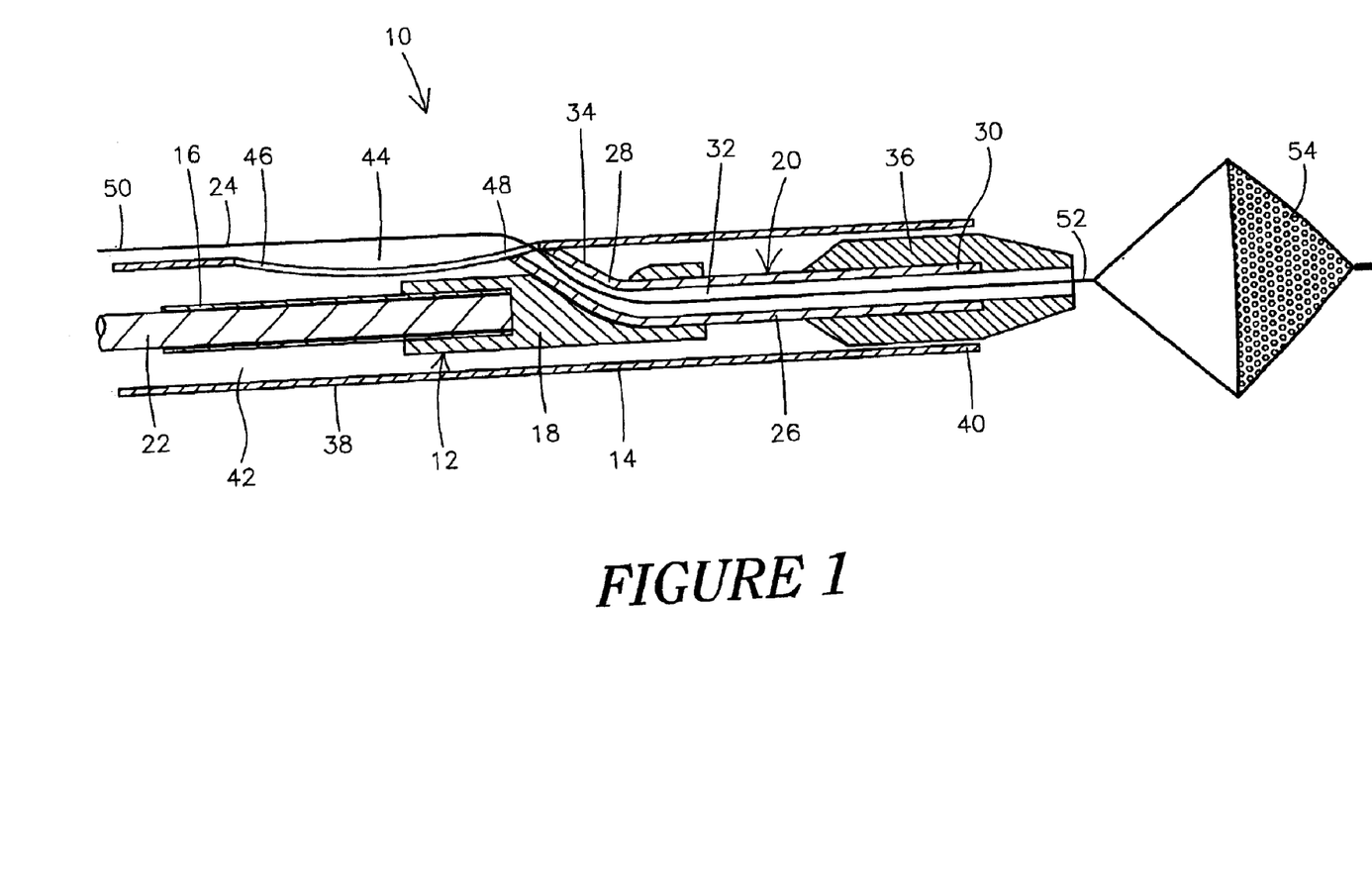
FIG. 1 is a cross sectional view of a filter retrieval catheter in an arrangement suitable for advancement through the vasculature.

FIG. 1 is a cross sectional view of a filter retrieval and delivery catheter 10 in an arrangement suitable for advancement through the vasculature. In an embodiment, a filter retrieval catheter 10 may comprise an inner shaft 12 slidably disposed within an outer sheath 14.

Inner shaft 12 may include a proximal end 16, a mid-region 18, and a distal end 20. Proximal end 16 may comprise an elongate tube. The elongate tube may be comprised of materials including, but not limited to, thermoplastics, high performance engineering resins: fluorinated ethylene propylene (FEP), polyethylene (PE), polypropylene (PP), polyvinylchloride (PVC), polyurethane, polytetrafluoroethylene (PTFE), polyetherether ketone (PEEK), polyimide, polyamide, polyphenylene sulfide (PPS), polyphenylene oxide (PPO), polysufone, nylon, perfluoro(propyl vinyl ether) (PFA), metals: stainless steel, nickel alloys, nickel-titanium alloys, and combinations thereof.

Proximal end 16 may be held to secure inner shaft 12 relative to outer sheath 14, for example be a lock wire 22. Alternatively, inner shaft 12 may be held in place relative to a guidewire 24. According to this embodiment, movement of guidewire 24 results in substantially similar movement of inner shaft 12. Moreover, movement of either guidewire 24 or inner shaft 12 may occur independently of movement of outer sheath 14.

Mid-region 18 may comprise an opening on each of two opposite ends. The openings may be appropriate for coupling mid-region 18 to proximal end 16 and distal end 20. Mid-region 18 may comprise a polymer or metal, including those listed above. In an exemplary embodiment, mid-region 18 comprises polyethylene.

Distal end 20 may comprise a tubular member 26 having a proximal region 28, a distal region 30, and a lumen 32 extending therethrough. Lumen 32 may be a guidewire lumen adapted for housing guidewire 24. Distal end 20 may comprise polyimide. Alternatively, distal end 20 may comprise materials similar to those listed above. Tubular member 26 is coupled to mid-region 18. For example, tubular member 26 may be disposed within an opening within mid-region 18 and bend to exit a second opening within mid-region 18. The bend in tubular member 26 when exiting mid-region 18 may define a port 34 that may be disposed at proximal region 28. A tip 36 can be disposed at distal region 30 of tubular member 26. Tip 36 is comprised of generally soft or atraumatic materials. For example, tip 36 may be comprised of materials including polymers. In addition, tip 36 may be comprised of materials similar to those listed above.

Outer sheath 14 may be disposed around inner shaft 12. Outer sheath 14 may be comprised of materials including, but not limited to, metals, alloys, nickel alloys, nickel titanium alloys, polymers, and combinations thereof. Alternatively, outer sheath 14 may be comprised of materials similar to those listed above.

Outer sheath 14 includes a proximal end 38, a distal end 40, and a lumen 42 extending therethrough. Lumen 42 is sized to allow inner shaft 12 to be slidably disposed therein.

Outer sheath 14 may include an opening 44. Opening 44 can be, for example, about 2 inches long. Opening 44 can be, for example, less than about 4 inches long. Opening 44 may further comprise a proximal region 46 and a distal region 48. In an exemplary embodiment, inner shaft 12 is disposed within lumen 42 such that port 34 is disposed substantially proximate opening 44.

Guidewire 24 may further include a proximal end 50 and a distal end 52. An embolic protection device 54, such as a distal protection filter, may be disposed at distal end 52. Embolic protection device 54 is adapted to prevent embolic debris from travelling away from a treatment site. According to this embodiment, embolic protection device 54 can substantially prevent embolic debris from occluding a blood vessel down stream from a treatment site.

Catheter 10 may be used as a filter retrieval catheter or a filter delivery catheter. When used to retrieve embolic protection device 54, catheter 10 is configured relative to guidewire 24 and inner shaft 12 is configured relative to outer sheath 14. As to configuring catheter 10 relative to guidewire 24, catheter 10 is generally passed over guidewire 24. According to this embodiment, guidewire 24 passes through lumen 32 of tubular member 26, through port 34, and through opening 44. Proximal end 50 of guidewire 24 extends proximally out of outer sheath 14 at opening 44. Distal end 52 of guidewire 24 extends distally out of tip 36 of distal region 30 of inner shaft 12.

When configured for retrieving embolic protection device 54 (or when generally configured for advancing through the vasculature) guidewire 24 may be locked relative to inner shaft, for example by locking wire 22. Moreover, guidewire 24 is generally disposed at a location near distal region 48 of opening 44 (as shown in FIG. 1). Disposing guidewire 24 near distal region 48 of opening 44 may be advantageous when using catheter 10 for retrieval. For example, positioning guidewire 24 near distal region 48 during retrieval (or generally during advancement of catheter 10 through the vasculature) makes available space for guidewire 24 to shift (proximally) within opening 44. This feature is important because guidewire 24 and inner shaft 12 may be locked. Thus, allowing space for guidewire 24 to proximally shift may allow movement or shifting of inner shaft 12 relative to sheath 14 (as described in more detail below).

As to configuring inner shaft 12 relative to outer sheath 14, inner shaft 12 may be oriented in a first position (as shown in FIG. 1). In the first position, inner shaft 12 is positioned distally within sheath 14 such that at least a portion of tip 36 extends out from outer sheath 14. In an exemplary embodiment, a tapered portion of tip 36 extends out of outer sheath 14 when inner shaft 12 is in the first position. Generally, the first position is appropriate for advancing catheter 10 through the vasculature and provides a generally tapered or atraumatic distal end to catheter 10.

Retrieval of embolic protection device 54 may then be accomplished by advancing catheter 10 through the vasculature to a position near embolic protection device 54 (for example, as shown in FIG. 1). Once located near embolic protection device 54, inner shaft 12 can be shifted from the first position to a second position. Shifting can occur by advancing sheath 14 distally relative to inner shaft 12. Shifting inner shaft 12 to the second position results in sheath 14 moving distally over inner shaft 12 such that tip 36 is disposed a distance proximally of distal end 40 of sheath 14 (as shown in FIG. 2).

Because guidewire 24 may be locked relative to inner shaft 12, shifting the position of inner shaft 12 results in shifting of guidewire 24 relative to sheath 15. In general, when inner shaft 12 shifts to the second position, guidewire 24 shifts such that it becomes disposed near proximal end 46 of opening. Because embolic protection device 54 is coupled to guidewire 24, shifting inner shaft 12 to the second position results in sheath 14 passing distally over at least a portion of embolic protection device 54 (as shown in FIG. 2). When at least a portion of embolic protection device 54 is disposed within sheath 14, catheter 10 (and, thus, embolic protection device 54) may be removed from the vasculature.

Catheter 10 may also be used to deliver embolic protection device 54. For example, inner shaft 12 may be in the second position (as shown in FIG. 2) and advanced through the vasculature. While advancing, embolic protection device 54 may be at least partially collapsed within sheath 14. Upon reaching a desired location, sheath 14 may be shifted (in the proximal direction) relative to inner shaft 12 and guidewire 24 such that embolic protection device 54 emerges from distal end 40 of sheath 14. Generally, embolic protection device 54 is designed to be self-expanding such that when device 54 emerges from sheath 14 it assumes the expanded configuration appropriate for filtering embolic debris. Thus, the shift of sheath 14 in the proximal direction allows embolic protection device 54 to expand and be delivered. Once embolic protection device 54 is delivered, catheter 10 may be removed from the vasculature.

Figure 2:
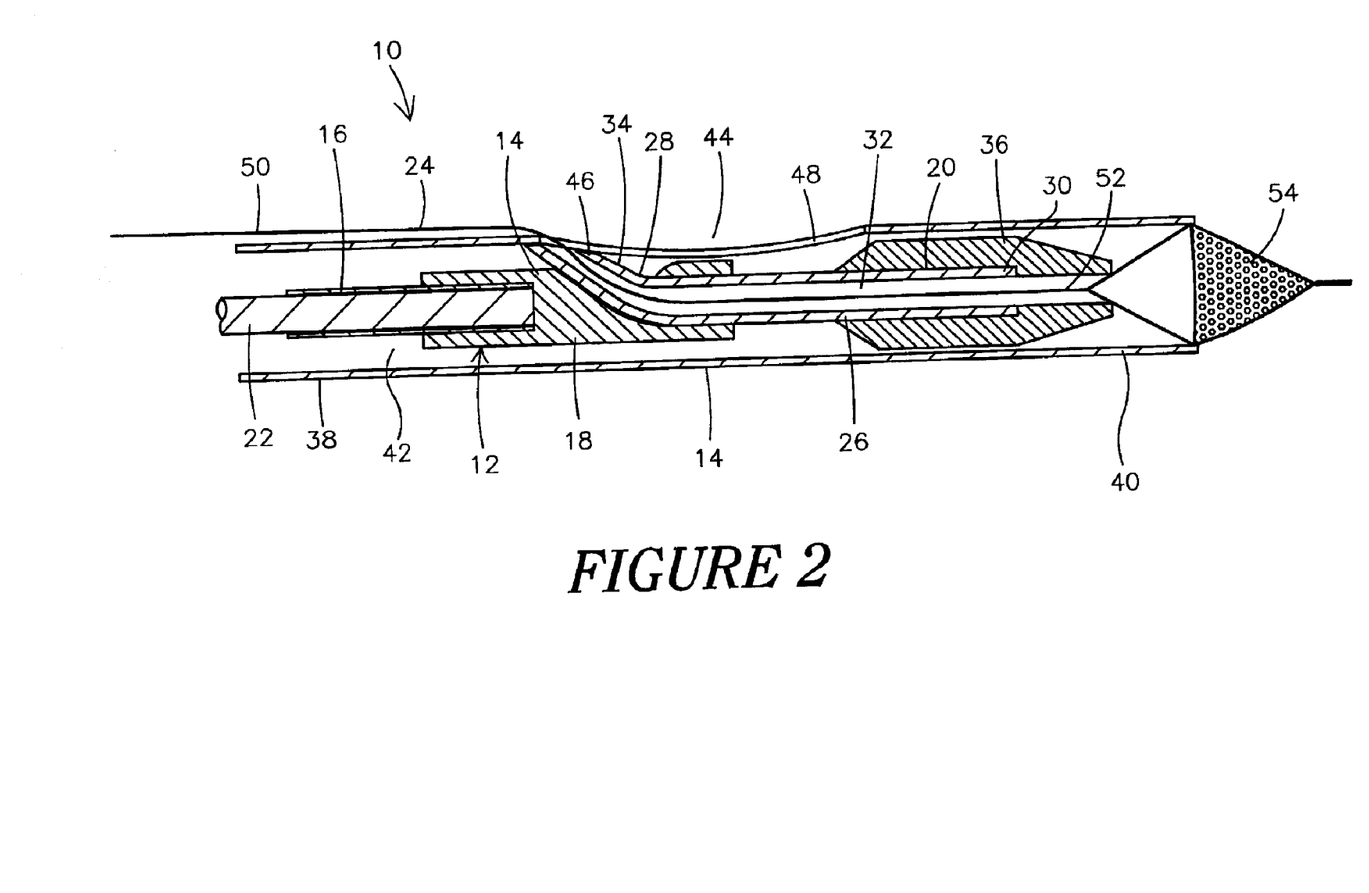
FIG. 2 is a cross sectional view of a filter retrieval catheter in an arrangement suitable for removal from the vasculature.

FIG. 2 is a cross sectional view of a filter retrieval catheter in an arrangement suitable for removal from the vasculature. Inner shaft 12 can be shifted from the first position to a second position relative to outer sheath 14 as shown. In the second position tip 36 may be substantially contained within lumen 42 of outer sheath 14. In addition, a portion of embolic protection device 54 may be disposed within outer sheath 14 after shifting from the first position to the second position. Shifting results in inner shaft 12 (specifically proximal region 28 and/or port 34) becoming disposed near proximal region 46 of opening 44. Subsequent to shifting, guidewire 24 may be secured in place during relative to sheath 14 and both can be removed proximally from the patient's vasculature.

Figure 3:
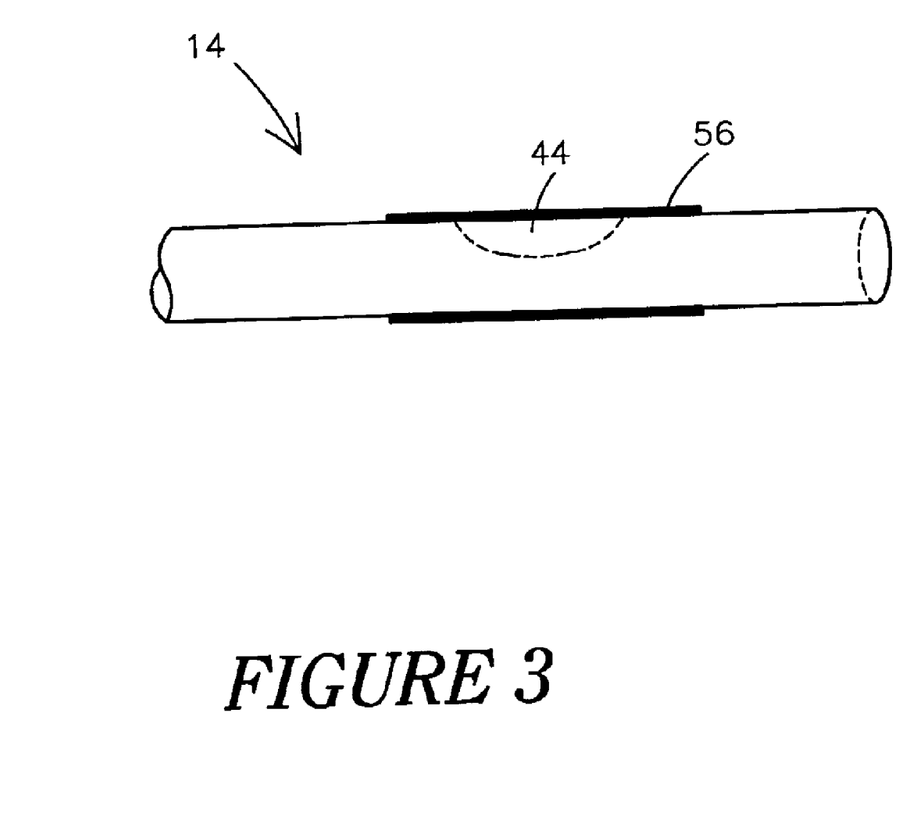
FIG. 3 is a side view of an alternate embodiment of an outer sheath further comprising a cover sheath.

FIG. 3 is a side view of an alternate embodiment of an outer sheath further comprising a cover sheath. A cover sheath 56 may be disposed on outer sheath 14 over opening 44. Cover sheath 56 may be comprised of a number of materials including polymers. Alternatively, cover sheath 56 may be comprised of materials similar to those listed above.

Cover sheath 56 may be coupled to outer sheath 14 in a number of differing manners. For example, cover sheath 56 may be coupled to outer sheath 14 by an adhesive. Alternative methods for coupling cover sheath 56 would be familiar to those of ordinary skill in the art.

Figure 4:
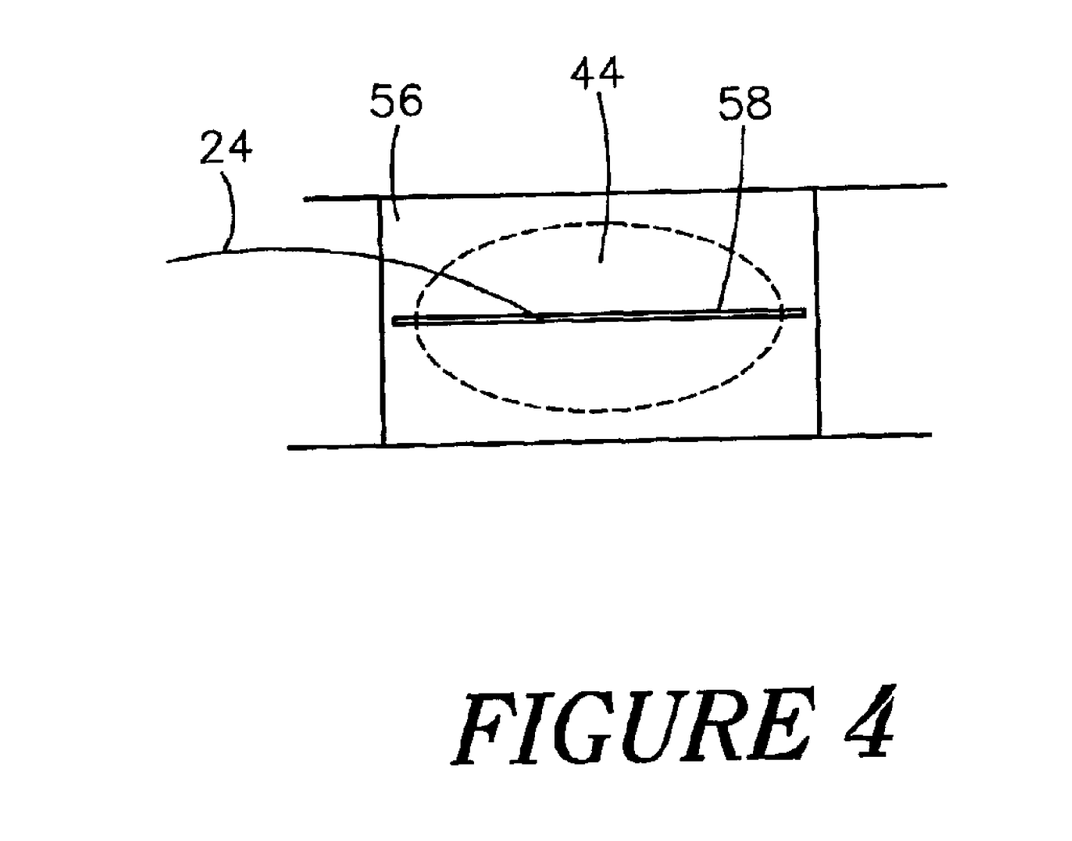
FIG. 4 is a top view of the cover sheath according an embodiment.

FIG. 4 is a top view of the cover sheath according an embodiment. Cover sheath 56 can further comprise a slot 58. Slot 58 may be sized appropriately for passage of guidewire 24. In addition, slot 58 may be substantially self-resealing. Self-resealing is understood to mean that slot 58 essentially prevents the passage of fluids therethrough but allows guidewire 24 to be moveable therein.

Figure 5:
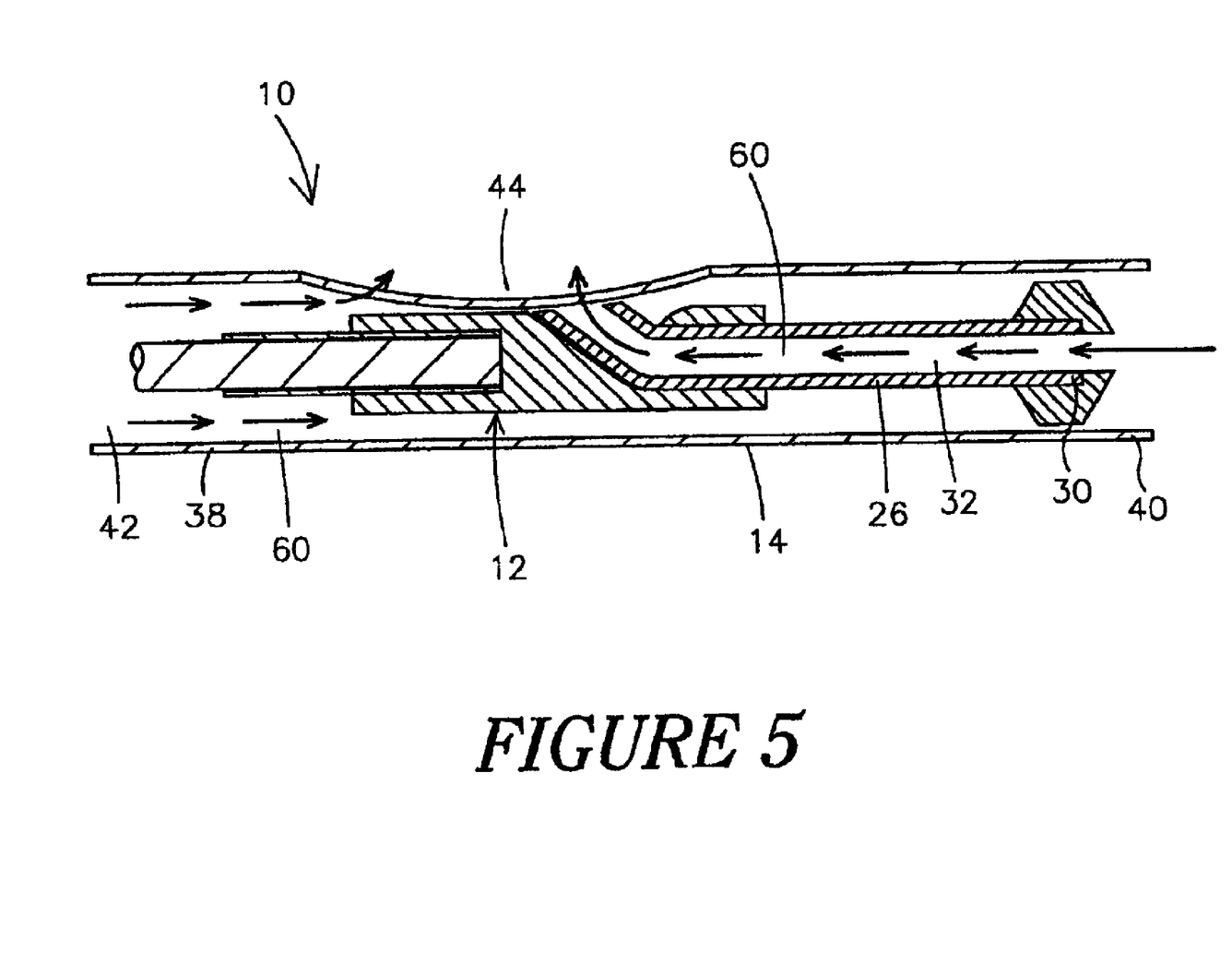
FIG. 5 is a cross sectional view for preparation of a filter retrieval catheter according to an embodiment of the invention.

FIG. 5 is a cross sectional view for preparation of a filter retrieval catheter according to an embodiment of the invention. Preparation of filter retrieval catheter 10 may include the step of substantially eliminating of air from vacant space 60 within inner shaft 12. Air may be substantially eliminated from vacant space 60 by flushing vacant space 60 with a fluid, such as saline. Alternative flushing mediums may be used without departing from the spirit of the invention.

To prepare filter retrieval catheter 10, fluid may be flushed through distal region 30 of tubular member 26 and throughout tubular member 26. Fluid can be additionally flushed through proximal end 38 of outer sheath 14, distal end 40 of outer sheath 14, and through opening 44. Flushing substantially eliminates air from vacant space 60.

Figure 6:
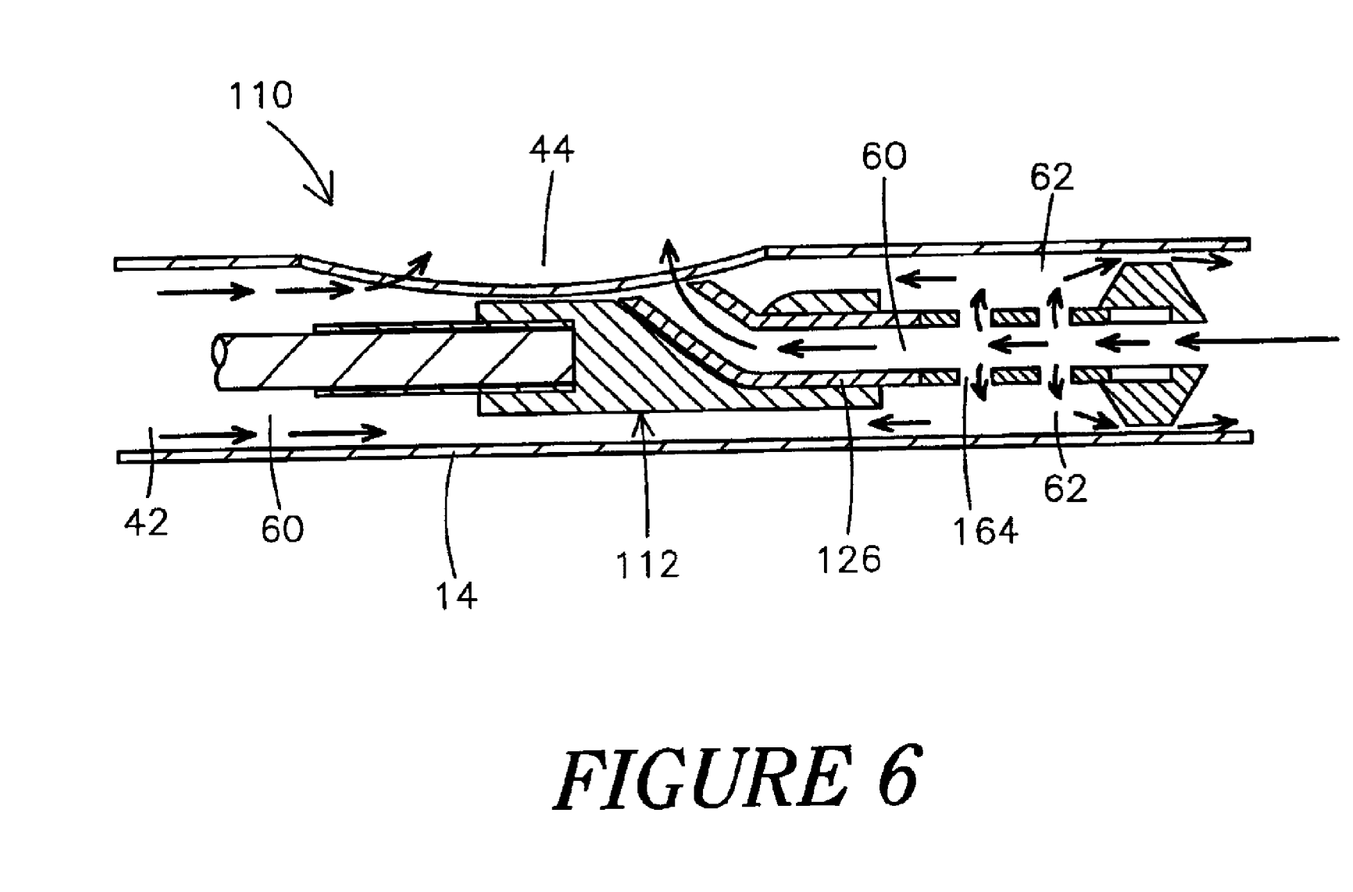
FIG. 6 is an alternate cross sectional view for preparation of a filter retrieval catheter according to an embodiment of the invention.

FIG. 6 is a cross sectional view for preparation of a filter retrieval catheter according to an embodiment of the invention. In addition to vacant spaces 60, distant vacant spaces 62 may be present. According to some embodiments of the invention, distant vacant spaces 62 may not be adequately flushed by the using the preparation strategy shown in FIG. 5.

To address this issue, an alternate filter retrieval catheter 110 may be constructed including an alternate inner shaft 112. Inner shaft 112 may comprise tubular member 126. Tubular member 126 can further comprise a plurality of flush holes 164. According to this embodiment, flushing fluid through inner shaft 112 and through tubular member 126 may result in substantial flushing of distant vacant spaces 62 by allowing fluid to be flushed through holes 164.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A catheter for retrieval of an embolic protection device, comprising:
    an inner shaft including a tubular member;
    an outer sheath including a side opening, the outer sheath disposed over the inner shaft;
    the tubular member including a proximal region, a port disposed near the side opening, a distal region, and a tip disposed at the distal region;
    the tubular member is slidable within the outer sheath; and
    wherein the inner shaft includes a plurality of openings disposed on the wall of the tubular member in addition to the port.

2. The catheter in accordance with claim 1, wherein the openings in the inner shaft are a plurality of flush holes.

3. The catheter in accordance with claim 1, wherein the tip is tapered.

4. The catheter in accordance with claim 1, wherein the length of the side opening is between about one to four inches in length.

5. The catheter in accordance with claim 1, further comprising a cover sheath disposed about the outer sheath.

6. The catheter in accordance with claim 5, wherein the cover sheath substantially covers the side opening.

7. The catheter in accordance with claim 5, wherein the cover sheath further comprises a slot.

8. The catheter in accordance with claim 7, wherein the slot is substantially self-resealing.

9. The catheter in accordance with claim 7, wherein the slot is adapted to allow passage of the guidewire therethrough.

10. A retrieval catheter and embolic protection device, comprising:
    an inner shaft including a tubular member;
    the tubular member including a proximal region, a port disposed near the proximal region, a distal region, and a tip disposed at the distal region;
    an outer sheath including a side opening;
    a cover sheath disposed over the outer sheath;
    a guidewire having a distal end;
    an embolic protection device disposed at the distal end of the guidewire;
    the guidewire is adapted to be disposed within the lumen of the inner shaft and pass through the cover sheath; and
    wherein the inner shaft defines a plurality of openings in addition to the port.

11. The catheter in accordance with claim 10, wherein the openings in the inner shaft are a plurality of flush holes.

12. The catheter in accordance with claim 10, wherein the tip is tapered.

13. The catheter in accordance with claim 10, wherein the length of the side opening is about one to four inches.

14. The catheter in accordance with claim 10, wherein the cover sheath substantially covers the side opening.

15. The catheter in accordance with claim 10, wherein the cover sheath further comprises a slot.

16. The catheter in accordance with claim 15, wherein the slot is substantially self-resealing.

17. A method for retrieving an embolic protection device, comprising the steps of:
    providing a guidewire into a vascular region of a patient, the guidewire having a distal end and an embolic protection device disposed at the distal end;
    providing a retrieving catheter comprising an inner shaft and an outer sheath, the outer sheath including a side opening; wherein the inner shaft includes a tubular member having a proximal region, a port disposed near the side opening in the outer sheath, a distal region, and a tip disposed at the distal region; and wherein the inner shaft further comprises a plurality of flush holes;
    placing the inner shaft in a first position relative to the outer sheath;
    advancing the catheter over the guidewire to a position near the embolic protection device;
    locking the guidewire relative to the inner shaft;
    shifting the inner shaft and the guidewire to a second position relative to the outer sheath, wherein shifting to the second position results in at least a portion of the embolic protection device being disposed within the outer sheath; and removing the catheter and guidewire from the vascular region.

18. The method in accordance with claim 17, further comprising the step of flushing fluid through the tubular member.

19. The method in accordance with claim 18, wherein the fluid substantially eliminates air from vacant space within the catheter.

20. The method in accordance with claim 19, wherein the fluid substantially eliminates air from distant vacant spaces within the catheter.

21. The method in accordance with claim 17, wherein the tip is tapered.

22. The method in accordance with claim 17, wherein the length of the side opening is between about one to four inches.

23. The method in accordance with claim 17, wherein the cover sheath substantially covers the side opening.

24. The method in accordance with claim 23, wherein the cover sheath further comprises a slot.

25. The method in accordance with claim 24, wherein the slot is substantially self-resealing.

26. The method in accordance with claim 17, wherein the embolic protection device includes a filter.

27. A method for delivering an embolic protection device, comprising the steps of:

providing a delivery catheter comprising an inner shaft and an outer sheath, the outer sheath including a side opening; wherein the inner shaft includes a tubular member having a proximal region, a port disposed near the side opening of the outer sheath, a distal region, and a tip disposed at and a plurality of openings beside the port, configuring the inner shaft such that at least a portion of the tip extends distally out of a distal end of the outer sheath;

disposing a guidewire within a portion of the inner shaft, the guidewire including an embolic protection device coupled thereto, wherein at least a portion of the embolic protection device is collapsed within the outer sheath;

advancing the catheter through a vascular region of a patient to a desired location;

shifting the outer sheath proximally relative the inner shaft and the guidewire such that the embolic protection device emerges from the distal end of the outer sheath; and removing the delivery catheter from the vascular region of the patient.

* * * * *

UNITED STATES PATENT AND TRADEMARK OFFICE
CERTIFICATE OF CORRECTION

PATENT NO. : 6,997,938 B2  
APPLICATION NO. : 10/075485  
DATED : February 14, 2006  
INVENTOR(S) : Ling Wang et al.

Page 1 of 1

It is certified that error appears in the above-identified patent and that said Letters Patent is hereby corrected as shown below:

Col. 8 Claim 27, line 8, after "a tip disposed at" add --the distal region--

Signed and Sealed this

Twenty-sixth Day of December, 2006

JON W. DUDAS  
*Director of the United States Patent and Trademark Office*